(12) United States Patent
Cook et al.

(10) Patent No.: US 8,364,222 B2
(45) Date of Patent: Jan. 29, 2013

(54) IMAGING APPARATUS AND METHOD

(75) Inventors: Richard James Cook, London (GB); Timothy Frederick Watson, London (GB); Frederic Festy, London (GB)

(73) Assignee: King's College London, London (GB)

( * ) Notice: Subject to any disclaimer, the term of this patent is extended or adjusted under 35 U.S.C. 154(b) by 389 days.

(21) Appl. No.: 12/678,646

(22) PCT Filed: Sep. 19, 2008

(86) PCT No.: PCT/GB2008/003174
§ 371 (c)(1),
(2), (4) Date: May 19, 2010

(87) PCT Pub. No.: WO2009/037464
PCT Pub. Date: Mar. 26, 2009

(65) Prior Publication Data
US 2010/0256469 A1 Oct. 7, 2010

(30) Foreign Application Priority Data
Sep. 19, 2007 (GB) .................................. 0718291.8

(51) Int. Cl.
*A61B 5/00* (2006.01)

(52) U.S. Cl. ......................... 600/323; 600/109; 600/181

(58) Field of Classification Search .................. 600/109, 600/323, 352, 454, 458, 181
See application file for complete search history.

(56) References Cited

U.S. PATENT DOCUMENTS 6,110,106 A * 8/2000 MacKinnon et al. ......... 600/181
7,460,248 B2 * 12/2008 Kurtz et al. .................. 356/521

FOREIGN PATENT DOCUMENTS

| WO | WO 9822018 A   | 5/1998  |
| WO | WO 9822018 A1 * | 5/1998  |
| WO | WO 9966830 A   | 12/1999 |
| WO | WO 0115597 A   | 3/2001  |

OTHER PUBLICATIONS

International Search Report for PCT/GB2008/003174 (WO2009/037464 A1), Issued Jan. 15, 2009.

* cited by examiner

*Primary Examiner* — Clayton E Laballe
*Assistant Examiner* — Warren K Fenwick
(74) *Attorney, Agent, or Firm* — Banner & Witcoff, Ltd

(57) ABSTRACT

The invention relates to an apparatus and a method for imaging the vascular structure and vascular blood flow of an organ or tissue and, in particular, relates to a selective wavelength epi-illumination endoscopic imaging apparatus to image vascular tissues and real time capillary blood flow in vivo. The invention also relates to determining the blood oxygen content of the organ or tissue.

25 Claims, 5 Drawing Sheets

IMAGING APPARATUS AND METHOD

The invention relates to an apparatus and a method for imaging the vascular structure and vascular blood flow of an organ or tissue and, in particular, relates to a selective wavelength epi-illumination endoscopic imaging apparatus to image vascular tissues and real time capillary blood flow in vivo. One possible application of this apparatus and method is vascular characterisation in soft tissue lesion diagnosis.

Endoscopy has long been used in medicine to image inaccessible regions of the human body for non-invasive diagnostic and therapeutic interventions, revolutionising diagnosis and management of numerous conditions (1). The majority of current medical endoscopy involves wide field, white-light, epi-illumination colour imaging (constant illumination or reconstructed RGB scanning), the images being a summation of surface and sub-surface reflections (2). Poor contrast within most observed tissues makes individual cell, tissue and tumour boundary definition difficult without vital (in vivo) staining or post biopsy histopathological processing. The former technique, often referred to as chromo-endoscopy, often employs topical methylene blue or iodine, although some techniques selectively prepare damaged tissues with acetic acid or proteases (3-6). Elegant examples of vitally stained deranged nuclei have been demonstrated in vivo from oesophageal tumours with the aid of magnifying endoscopes (up to ~x80-100) (4; 5; 7). The potential of endoscopic optical coherence tomography, spectroscopy and the enhanced contrast imaging benefits of confocal systems in trying to discriminate low contrast structures have also been demonstrated (6; 8).

Fluorescence can also be employed to highlight tumour tissue with varying degrees of success. Abe et al. (2000) described the LIFE-GI system (Light Induced (auto) Fluorescence Endoscopy) for gastro-intestinal tumour auto-fluorescence detection (9). However, the method is less able to identify undifferentiated cancers, which can invade in a more dispersed manner without altering the mucosal thickness (9). Bhunchet et al. (2002) showed that after intravenous fluorescein, early gastric cancer fluorescence delineated the associated stroma and early cancer margins (10). However, the danger of severe Type I hypersensitivity (anaphylactic) reactions to the use of IV fluorescein (0.05% serious & 21% mild side effects), renders the process less attractive in clinical use (11).

Microendoscopy was initially developed for uterine examinations (colpohysteroscopy) in the late 70's and developed further for laryngoscopy in the late 90's (12). Watson et al. (2002) developed a dual confocal and epi-illumination contact micro-endoscopy instrument via a Hopkins pattern colpohysteroscope, capable of vascular imaging, demonstrating regular capillary networks in oral lingual and labial mucosa conforming to twisted spiral patterns (8). Yao et al. used magnifying endoscopy to show similar, regular subepithelial capillary networks in non-cancerous gastric mucosa, noting normal architecture variations throughout the stomach; the body showing a honeycomb network with collecting venules, whereas the antrum showed a coil-shaped network pattern (13).

The colour change observed macro-endoscopically in white light illumination correlates well with vascular architecture and density in early gastric cancers (13-15). Differentiated carcinomas show well demarcated areas of proliferating irregular vessels of varying calibres, replacing the normal mucosa capillary pattern (15-18) whereas undifferentiated lesions show ill-defined areas of relative capillary density loss (13).

Kumagai Y. et al. (2002) similarly noted that in more advanced, invasive oesophageal carcinomas, the capillary loop patterns showed progressive dilatation and elongation until complete replacement by tumour vessels occurred in advanced tumours involving the sub mucosa (5). Topical adrenaline causes normal (gastric) mucosa to blanche from red to white reflecting expected ischaemia and vasoconstriction, while cancerous lesions show an enhancement of tumour microvessels after identical exposure, suggesting an escape from normal catecholamine control in the tumour vasculature (19; 20).

Using red and green images obtained from an electronic endoscopic image, a comparative algorithm allowed Tsuji S. et al (1991) to calculate a haemoglobin content value by pixel for their co-localised images of gastric ulcers. Haemoglobin and thus vascular lesion content fell in active ulceration and rose in actively healing ulcers when compared to normal mucosa (21). Using a similar narrow band illumination imaging technique and a laser scanning microscope, Nakayoshi T et al. (2004) constructed 3D images of gastric tumour microvessels (22).

A plethora of histopathological assays have demonstrated that angiogenesis (the formation of new blood vessels; neovascularisation) is essential for oral malignant lesion development and progression and can reflect dysplasia—carcinoma in situ—neoplasia and invasion/progression (23-32). However, few, if any, direct in vivo imaging studies are reported confirming this finding.

Upile et al. (2006) claim the first use of an un-filtered white light epi-illumination Hopkins pattern micro-endoscope to qualitatively observe micro-vascular patency and flow within a free jejunal graft, translocated to the pharynx, monitoring for intra operative pedicle thrombosis (33).

The prior art presents an interesting conundrum, as by definition, the biopsy free imaging configuration is that of a classical reflection mode instrument. Reflection mode instruments generally give poor contrast between tissues even using the higher magnification endoscopes noted by some authors. It is unclear how to obtain superior contrast of vascular tissue.

An object of the present invention is to provide an imaging apparatus and method for improved imaging of vascular tissue and capillary blood flow.

The present invention provides an imaging apparatus for imaging the vasculature of an organ or tissue comprising:
  a light source for illuminating the organ or tissue;
  a lens or lens apparatus mounted within a housing to collect light from the illuminated organ or tissue; and
  an image capturing device to image the green wavelengths of the light.

The present invention also provides a method for imaging the vasculature of an organ or tissue comprising:
  illuminating the organ or tissue;
  collecting the light from the organ or tissue; and
  imaging the green wavelengths of the collected light.

The invention only uses the green wavelengths of the light for imaging. This allows much better contrast to be obtained for vascular tissue allowing the vasculature to be well defined on images. The use of green light also allows the visualisation of individual red blood cells (RBCs) within the vasculature. This can be used to measure real time blood flow in vivo by measuring the movement of particular RBCs over time.

The inventors hypothesise, without wanting to be held to any particular theory as being responsible for the results, that the increased contrast obtained using green light is due to the light absorption characteristics of haemoglobin (Hb). Haemoglobin is the red oxygen transporting iron-containing metalloprotein contained in mammalian RBCs. The inventors hypothesise that RBCs, as simplified pigment-containing 6-8 μm biconcave disks, behave as optical filters, blocking passage of all but long wavelengths of light, both entering and reflected back from deeper tissues and interfaces. This would explain why using green light provides good contrast in vascular tissue as the RBCs strongly absorb green light, thus appearing with a dark outline, whilst surrounding tissue allows this wavelength of light to pass therethrough.

The organ or tissue can be any organ or tissue that can be accessed from outside the body. For example, this could be the skin, mouth, the organs of the gastrointestinal tract, respiratory tract, genitourinary tract and the female reproductive system. This also includes imaging internal body cavities through a small incision, for example, the abdominal and pelvic cavities, the interior of a joint and organs of the chest. For example, it is possible to image the brain, eye, spine, bladder, kidneys, liver, pancreas and other such organs. This also includes during pregnancy to image the amnion, fetus and umbilical cord.

The vasculature is the blood containing circulatory system of the tissue or organ. This includes the arteries, arterioles, capillaries, venules and veins. Preferably, the imaging apparatus is for imaging the capillaries.

The light source can be any suitable light source for illuminating an organ or tissue. Preferably, the light source is positioned at a distance from the lens and the organ or tissue and light is transmitted to the organ or tissue by a light guide, thereby illuminating the organ or tissue. The light guide can be any suitable device for guiding light from the light source to the organ or tissue, for example, an optical fibre or a fibre optic cable.

The light source can emit electromagnetic radiation over a broad spectrum of wavelengths and is not limited to just the visible spectrum. For example, a standard endoscopic light source may emit wavelengths in the infrared and ultraviolet ranges. Suitable light sources which emit primarily white light (but also some other wavelengths) are well known to those skilled in the art. The light source must emit green wavelengths of light, although it can also emit other wavelengths. Green wavelengths of light are defined as being between 490 nm and 590 nm. The light source can emit light over a continuous spectrum of green wavelengths or alternatively, it can emit green light at one discrete wavelength, a number of discrete wavelengths, a range of wavelengths or a number of ranges of wavelengths. Accordingly, the following ranges are not meant to imply continuous emission of wavelengths throughout the range although this is also encompassed. Preferably, the light source emits light between about 490 nm and about 590 nm; more preferably between about 500 nm and about 570 nm; even more preferably between about 520 nm and about 560 nm; and most preferably, at about 540 nm.

The lens mounted within a housing can be any suitable lens to collect light from the illuminated organ or tissue. This can be a lens designed for contact or in vivo work. Such assemblies are well known to those skilled in the art. Preferably, the lens mounted within a housing is an endoscope. Endoscopes are medical instruments for looking inside the body and are well known to those skilled in the art.

The light source may illuminate the organ or tissue via the endoscope. When the light source is positioned at a distance from the lens and the organ or tissue and light is transmitted to the organ or tissue using a light guide, the light guide is preferably positioned within the endoscope.

Once the light has been collected by the lens mounted within the housing it is transmitted to an image capturing device to image the green wavelengths of the light. This can be any suitable image capturing device. Such image capturing devices are well known to those skilled in the art, for example, CCD (charge-coupled device) cameras and active pixel sensor imagers (also known as CMOS sensors). Preferably, the image capturing device is a CCD camera. Preferably the CCD camera is cooled.

The image capturing device is used to image the green wavelengths of light, that is to say, to capture the green wavelengths of light and to generate an image therefrom. In one embodiment of the apparatus, the light emitted from the light source is white light or contains other wavelengths of light other than simply green light. In this embodiment, it is necessary to ensure that the image capturing device only detects the green light. For example, only green light could be allowed to pass into the image capturing device by using an optical filter which allows only green light to pass through whilst absorbing or reflecting other wavelengths of light. Alternatively, the optical filter could be contained within the image capturing device itself. Optical filters are well known to those skilled in the art. For example, absorptive filters, dichroic filters, monochromatic filters, green pass filters or long pass filters (which allows green and all longer wavelengths of light to pass through) could be used. Preferably, a green pass or a monochromatic filter is used. Preferably, the filter allows light to pass through which has a wavelength of between about 490 nm and about 590 nm, more preferably, between about 500 nm and about 570 nm, even more preferably, between about 520 nm and about 560 nm and most preferably, about 540 nm.

In an alternative embodiment, the light emitted by the light source is green light or a particular wavelength or wavelengths of green light. In this embodiment, there would be no need for a filter as the light passing into the image capturing device from the lens would be of green wavelength. Alternatively, a filter could be used to narrow the range of green wavelengths passing into the image capturing device.

Preferably, the image capturing device is connected to a computer so that the images can be stored and processed using the computer. This is important for real time imaging, which typically uses about 24 frames per second, and allows easy storage of the images, immediate display of the images and allows them to be easily reviewed at a later time.

The imaging apparatus can be used to image the vasculature of an organ or tissue in any organism that has haemoglobin containing RBCs within its vasculature. For example, humans, primates, mammals, fish and most vertebrates could be studied. Preferably, the imaging apparatus is for use on humans and mammals and more preferably, for use on humans.

The apparatus and method according to the invention as described above allows improved imaging of vascular tissue through the use of green light to maximise the contrast between the RBCs and surrounding tissue. For example, this can be used to analyse the vasculature and blood flow in soft tissue lesions, newly implanted organs, in grafts (e.g. skin grafts) and blood flow in the umbilical cord in cases of fetal distress to name but a few applications. One of the major advantages of the invention is that it provides a multi-purpose tool which can be used in a large number of applications in both human and veterinary medicine.

The apparatus and method of the present invention can also be used in conjunction with additional apparatus to allow blood oximetry; the measurement of the oxygenation of blood.

The most popular technique used to measure blood oxygenation is pulse oximetry. This is based on the absorption ratios of oxygenated and deoxygenated haemoglobin at two different wavelengths. The absorption characteristics of blood differs significantly in the red and infrared region of the spectrum depending on its oxygenation state. Oxygenated haemoglobin absorbs more infrared light (850-1000 nm) and lets more red light (600-750 nm) pass through than deoxygenated haemoglobin. By monitoring the difference between these two ratios over time and taking into account background "noise" due to the absorption of other tissue, a fairly accurate reading of blood oxygenation can be obtained. However, this technique suffers from a number of problems, mainly due to the fact that it largely relies on ensemble measurement (a few millimeter square) recorded by a large photodiode. Those problems include the following:

1. the geometry of the commonly used device results in light emitted by the LED which surround the light sensor, causing reading errors from mal-positioned sensors (Penumbra Effect) and direct light bleed-through;
2. single point measurement requires a long recording period (a few seconds) for background removal. During this period, multiple problems often occur, such as patient motion (venous motion) and irregular blood flow (venous pulsation and congestion), which can lead to erroneous readings; and
3. pulse oximetry cannot provide any information on the structure of blood vessels due to the lack of image provided by this single point technique. The oxygenation measurement is therefore an average and can miss entirely any problems in small capillaries.

Another object of the present invention is to provide an apparatus and method to allow the direct imaging of vasculature and to map the precise blood oximetry across this vasculature with unprecedented lateral resolution.

The present invention also provides the imaging apparatus described above (i.e. a light source for illuminating an organ or tissue; a lens mounted within a housing to collect light from the illuminated organ or tissue; and an image capturing device to image the green wavelengths of the light) further comprising a first optical filter to separate green wavelengths from the light and a second optical filter to separate red wavelengths in the light from infrared wavelengths in the light and two additional image capturing devices to image the red and infrared wavelengths of the light. Alternatively, the second optical filter can separate red wavelengths in the light from blue wavelengths in the light and the two additional image capturing devices image the red and blue wavelengths of the light.

As discussed above, the absorption characteristics of blood differs significantly across the visible and infrared region of the spectrum depending on its oxygenation state. Oxygenated haemoglobin absorbs more infrared light (850-1000 nm) and blue light (450 nm-500 nm), and lets more red light (600-750 nm) pass through than deoxygenated haemoglobin. By monitoring the difference between two of these ratios over time, a fairly accurate reading of blood oxygenation can be obtained.

Preferably, red and blue wavelengths of light are separated and monitored to determine the blood oxygenation. The inventors have surprisingly found that using red and blue wavelengths of light is as accurate as using red and infrared wavelengths of light. The advantage of using red and blue light rather than red and infrared is that the light used to illuminate the organ or tissue does not contain infrared wavelengths of light. The advantage of this is that the tissue or organ is not subjected to as much heat which could potentially damage the tissue or organ. Further, when haemoglobin is heated up it is converted into methemoglobin which has a different absorption spectrum compared to normal haemoglobin. Therefore, this affects the accuracy of the blood oxygenation measurement.

The present invention also provides the imaging method described above (i.e. illuminating an organ or tissue; collecting the light from the organ or tissue; and imaging the green wavelengths of the collected light) further comprising: separating the green, red and infrared wavelengths in the light; imaging each of the green, red and infrared wavelengths of the light; and calculating the oxygenation of the vasculature using the red and infrared images. Alternatively, the method can further comprise: separating the green, red and blue wavelengths in the light; imaging each of the green, red and blue wavelengths of the light; and calculating the oxygenation of the vasculature using the red and blue images.

This allows blood oximetry by measuring and mapping the blood oxygen content of the vasculature. The green light imaging part works in the same way as described above and allows an image of the vasculature to be produced. An image of the infrared and red wavelengths is also produced or an image of the blue and red wavelengths. Using the infrared and red images or the blue and red images, an instantaneous map of the blood oxygen content can be calculated which can then be correlated to the image of the vasculature. This allows determination of the blood oxygen content at any particular point on the vasculature image, and can even provide the oxygen content of particular RBCs.

In this embodiment of the invention, the light source which illuminates the organ or tissue must contain at least green, infrared and red wavelengths of light or at least green, blue and red wavelengths of light. Green light is defined as being between 490 nm and 590 nm; red light is defined as being between 600 nm and 750 nm; infrared light is defined as being between 850 nm and 1000 nm; and blue light is defined as being between 450 nm and 500 nm. As described above, the light source can emit light over a continuous spectrum of wavelengths or alternatively, it can emit light at one discrete wavelength, a number of discrete wavelengths, a range of wavelengths or a number of ranges of wavelengths in each particular band of light. Preferably, the light source does not emit infrared wavelengths of light.

As described above, the filters can be any suitable filters for selecting for the correct wavelengths of light and such filters are well known to those skilled in the art. For example, absorptive filters, dichroic filters or monochromatic filters could be used. Preferably, a dichroic filter is used.

For example, in one embodiment, the first filter may be a dichroic filter which reflects only green light from the collected light into the image capturing device set up for measuring green wavelengths. The second filter may be a dichroic filter which reflects only red light into the image capturing device set up for measuring red wavelengths whilst other wavelengths, including infrared and blue, pass through. The infrared or blue wavelengths in the transmitted light can be measured by an image capturing device set up to measure only infrared or blue wavelengths. Additionally, there may be filters on or in the image capturing devices to control exactly which wavelengths of light enter or are detected by the image capturing devices.

In another embodiment, a third optical filter may be present in order to give a user the maximum amount of control over the wavelengths of light passing into the image capturing devices. For example, in the embodiment described above, a third filter could be used to reflect all light except infrared or blue wavelengths. Infrared or blue wavelengths may then pass through the filter and into the infrared or blue image capturing device. Alternatively, the filter may reflect infrared or blue wavelengths into the infrared or blue image capturing device. This ensures that only the light of interest is entering any one of the image capturing devices which will help to reduce background. Again, there may additionally be filters on or in the image capturing devices to control exactly which wavelengths of light enter or are detected by the image capturing devices. For example, the first filter may reflect all green wavelengths of light into the image capturing device whilst an additional filter on or in the image capturing device ensure that only light of a wavelength of 540 nm is detected.

As will be appreciated by one skilled in the art, the wavelengths of light entering the image capturing devices can be controlled in a number of ways. These are: control of the wavelengths of light emitted by the light source; control of the wavelengths of light separated or reflected by the filters; and control of the light detected by the image capturing device, for example, by way of a filter on or in the image capturing device. Varying amounts of control can be applied at any particular stage. For example, with reference to green wavelengths of light, the light source may emit all wavelengths of light, the first filter may reflect wavelengths of between 520 nm and 560 nm towards the image capturing device, and a filter on or in the image capturing device ensures that only wavelengths of 540 nm are detected. One, some or all of these control means can be used to ensure only particular wavelengths of light are detected by the image capturing device. The preferred wavelengths of light that are detected by the various image capturing devices, however they are controlled, are as follows: for green light, preferably wavelengths of between about 490 nm and about 590 nm are detected, more preferably, between about 500 nm and about 570 nm, even more preferably, between about 520 nm and about 560 nm and most preferably, about 540 nm; for red light, preferably wavelengths of between about 600 nm and about 750 nm are detected, more preferably, between about 600 nm and about 700 nm, even more preferably, between about 640 nm and about 680 nm and most preferably, about 660 nm; for infrared light, preferably wavelengths of between about 850 nm and about 1000 nm are detected, more preferably, between about 900 nm and about 1000 nm, even more preferably, between about 890 nm and about 930 nm and most preferably, about 910 nm; and for blue wavelengths of light, preferably wavelengths of between about 450 nm and about 500 nm are detected, more preferably, between about 460 nm and about 490 nm, even more preferably, between about 470 nm and about 480 nm and most preferably, about 475 nm.

As described above, the two additional image capturing devices can be any suitable image capturing device for imaging the particular wavelengths of interest, i.e. green, red and infrared; or green, red and blue. Such image capturing devices are well known to those skilled in the art. Preferably, the imaging capturing devices are set up to have maximum sensitivity for the particular wavelengths of interest or only to be sensitive to the wavelength of interest. Preferably, the image capturing devices are CCD cameras. Preferably, the CCD cameras are cooled. The advantage of CCD cameras is that they allow images to be captured in real time with unprecedented optical resolution.

The oxygenation of the vasculature can be calculated in any suitable way using the infrared and red images or using the red and blue images. For example, the ratio between the infrared and red images can be calculated in a similar fashion to pulse oximetry to obtain a map of the blood oxygen content which can be correlated to the image of the vasculature. Alternatively, the ratio between the blue and red images can be calculated to obtain a map of the blood oxygen content which can be correlated to the image of the vasculature. Preferably, the image capturing devices are connected to a computer so that the images can be stored and processed using the computer. This is important for real time imaging, which typically uses about 24 frames per second, and allows easy storage of the images, immediate display of the images and allows them to be easily reviewed at a later time. Preferably, the computer is used for the determination of the blood oxygen content across the image of the vasculature. This is preferably as it may be necessary to use complex algorithms in determining the blood oxygen content. The above apparatus and method preferably measure the green, red and infrared images; or the green, red and blue images simultaneously. This allows the real time imaging to occur.

Preferably, the apparatus is calibrated and the method comprises a calibration step. This calibration ensures that the images can be overlaid to align corresponding points in each image to allow calculation of the oxygenation and assignment of that oxygenation value to a particular point on the vasculature.

The advantage of being able to measure and map blood oxygen content of the vasculature of an organ or tissue is that it allows measurement of blood oxygenation at particular points. This is useful for ensuring the a particular organ or tissue not only has a blood supply but also an oxygenated blood supply. For example, this can be used to ensure that newly implanted organs have a healthy oxygenated blood supply and allow areas of an organ to be identified which may not have an oxygenated blood supply. It can also be used to ensure sufficient oxygenated blood is present in grafts (e.g. skin grafts) and in the umbilical cord in cases of fetal distress. This apparatus and method can also be used in many other applications.

The invention will now be described by way of example only with reference to the accompanying figures in which:

FIG. 1 shows a schematic diagram of the flexible imaging arm used. Optical bench components were configured into a 3 jointed (Jt) frame supporting the Hopkins pattern colpohysteroscope (E) (Karl Storz UK). 45 degree surface reflecting mirrors (Mi) at the joints allowed articulation and axial rotation of the endoscope bevel to meet human tissue (S) comfortably. Adaptive optics (O) were necessary to collimate green epi-illumination reflected light (vascular imaging mode) from the 540 nm filtered source and the fluorescence illumination from the 488 nm fluorescence illumination source, introduced via a long pass dichroic (Di). The Yokogawa confocal head acted as a neutral density filter in epi-illumination mode but was essential for optical sectioned surface fluorescence imaging, all images being detected by monochrome CCD (CCD).

FIG. 2: Flow estimations were made by following particular aggregates of red blood cells along capillary loops (A to B) establishing distance (D) per number of frames at 24 fps. Size bar—100 microns.

FIG. 3 shows transmission imaging of a human blood film. The 8 micron diameter RBCs show enhanced contrast against unfiltered background illumination with progressive shortening of wavelength. In monochrome illumination (images paired vertically), haemaglobin within the cells appears darker in shorter wavelengths. The phospholipid bi-layer edge effects are progressively less marked with extension of wavelength. (All images X60/1.40 NA oil: illumination wavelengths: blue 436 nm, green 518 nm, red 600 nm)

FIG. 4 shows red blood cell films imaged against half-absorbing half-reflecting slide background imaged using blue 436 nm, green 518 nm, and red 600 nm wavelengths. Matched greyscale images are to the right, showing loss of contrast at the longest wavelength but contrast patterns were otherwise maintained in the reflection imaging system. No structural detail could be seen against the non-reflective backgrounds (left of 650 micron fields) further supporting transmission effects over reflected wavelengths as the likely mechanism of image generation. X60/1.4NA oil lens.

FIG. 5 shows three views of differing capillary architecture in the oral mucosa. A: Buccal mucosa—long twisted capillary loops taking origin from deeper feeding arterioles. B:—In keratinised attached gingival mucosa pinpoint tips of capillary loops only are visible—as they rise between epithelial rete processes. C:—In the papillae of the dorsal tongue (folds of mucosa visible top left of frame), branched twisted capillaries originating from the arcuate feeder vessels rising into the mucosal segment. Scale bar 250 µm.

FIG. 6 shows serial co-localised endoscopic images at times (minutes) after sub-cutaneous delivery of adrenaline containing local anaesthetic. Within five minutes of exposure, arterioles have shut down but a few small capillaries remain open in each field. From thirty to sixty minutes post injection the vasoconstriction effect resolves and the field of view more closely resembles the pre-exposure image. 1 mm field widths.

FIG. 7 is a graph showing changes in the mean vascularity of nine volunteers and control showing significant reduction of image frame vascular occupation when the adrenaline was introduced (unpaired t-tests)—unlike the control data, showing a minor dip and recovery to near normal between the 5th and 10th minute and significant differences between active and control groups at all but pre and 60 minutes (unpaired t-tests). Adrenergic vascular suppression of supply returns towards normal between the 30th and 60th minute.

Figure 10:
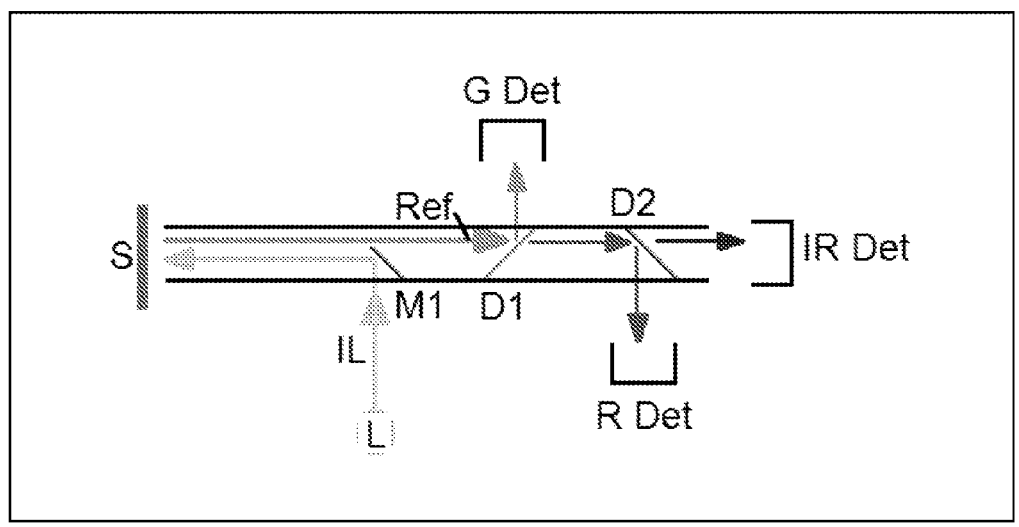

FIG. 10 shows a schematic of an apparatus according to the invention. In this schematic the following key is used: L—Multi wavelength illumination source; IL—Illumination beam; M1—Device to align epi-illumination beam onto sample; S—Specimen tissues; Ref—Reflection/transmission combined signal; D1—Dichroic 1—selects out green/yellow; G Det—Green selective detector; D2—Dichroic 2—selects out visible red; R Det—Visible red selective detector; and IR Det—Infrared selective detector.

EXAMPLE 1

The inventors hypothesise that the increased contrast obtained using green light is due to the light absorption characteristics of haemoglobin (Hb). The inventors hypothesise that RBCs, as simplified pigment-containing 6-8 µm biconcave disks, behave as optical filters, blocking passage of all but long wavelengths of light, both entering and reflected back from deeper tissues and interfaces. This would explain why using green light provides good contrast in vascular tissue as the RBCs strongly absorb green light, thus appearing with a dark outline, whilst surrounding tissue allows this wavelength of light to pass therethrough.

The inventors set out to test this imaging hypothesis and to apply the findings to oral mucosal investigations, using clinically well known 1:80,000 adrenaline based local anaesthetic agents to induce a controlled and time limited vasoconstriction to allow assessment of the apparatus and to assess the long held dental surgeons' belief that while the local analgesic effect lasts 2-3 hours, the vasoconstriction and thus relatively bloodless minor oral surgical operating field lasts less than one hour.

Materials and Methods:

In Vitro:

To investigate the initial hypothesis that high contrast RBCs imaging was in effect a transmission filtering effect, a series of images were acquired of human RBCs in both reflection and transmission illumination scenarios at red, green & blue wavelengths to compare images gained. Fresh heparinised human blood from a volunteer was diluted with an equal volume of sterile normal saline to avoid osmotic cell damage. A thin blood film was viewed (Olympus BX 60 microscope, Olympus UK, London, UK) in transmission (×20/0.80 oil, ×60/1.40 oil, ×100/1.30 oil) with monochromatic red, green and blue epi-illumination (blue 436 nm, green 518 nm, red 600 nm) from a 'Spectra master' light source (Perkin Elmer LSR, Cambridge, UK). Reconfiguration allowed reflection imaging using the same instrument but the blood films were re-made using slides with a 50% white (reflecting) and 50% matt black (non-reflecting) surfaces. Both greyscale (256 Houndsfield number—linear conversion without weighting) and colour images of the blood samples were obtained. The former were recorded using a constant parameter monochrome Cohu camera (4912 CCD camera, Cohu, Inc. San Diego, USA) whereas the latter were recorded using a Nikon digital camera (Coolpix 5000, Nikon, Japan).

In both transmission and reflection imaging modes, the greyscale difference in appearance of the RBCs against background wavelength was mathematically estimated by tracing and comparing the relative grey levels of ten areas representing RBCs and ten areas representing the background using Lucida 4.0 software (Lucida Analyse 4.0, Kinetic Imaging, Nottingham, UK). This relative data allowed for variation in energy introduced at each wavelength used.

Figure 1:
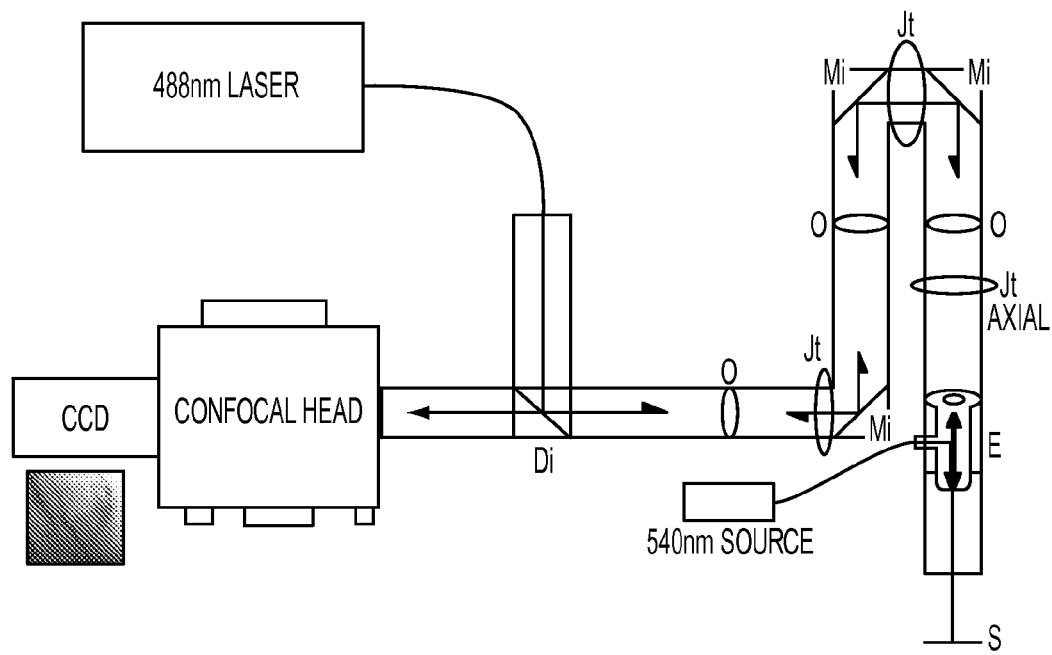

In Vivo:

The in vivo part of this study involved imaging of oral sub-mucosal vascular architecture via a dual confocal and epi-illumination contact micro-endoscopy instrument (see FIG. 1). In essence, rigid optical bench components were configured into a 3 part articulated frame supporting a Hopkins pattern colpohysteroscope (Karl Storz UK), using 45 degree surface reflecting mirrors to maintain optical axis alignment through the single plane joints. An axial rotation feature in the final arm allowed the endoscope bevel to meet human oral tissue comfortably. A long pass dichroic mirror separated 488 nm blue illumination from the excited fluorescence and (540+/−5 nm bandpass filter (Knight Optical, Harrietsham, UK) reflection images, detected by monochrome CCD passing through a Yokogawa confocal head; acting as a neutral density filter in epi-illumination mode, but essential for co-localised optical sectioned surface fluorescence imaging.

Nine medically fit volunteers underwent initial real time imaging of the lower labial mucosa with the instrument, using the 540 nm epi-illumination source. The area of mucosa imaged was outlined with a surgical skin marker, allowing review of the same local mucosa at set time intervals of 5, 10, 15, 30 and 60 mins after the co-localised administration of a known volume (<0.5 ml) of sub-cutaneous Xylotox (2% Lignocaine & 1:80,000 adrenaline) (Dentsply Ltd, Surrey, UK) via a conventional 27 gauge dental syringe.

Glycerol coupling was used to maintain optical integrity between the contact instrument and the labial mucosa. Movement of the instrument within the injected demarcated surface area was accepted as real-time video imaging allowed a survey of the vascular tissue architecture and alterations pre and post injection. Data was collected with the 4912 CCD Camera and recorded using AQM 6 software (AQM 6, Kinetic Imaging, Nottingham, UK). To examine the possible influence of injected fluid volume on vascular changes, imaging was repeated in one volunteer after an identical volume of plain normal saline was injected. Two still frames were selected from each 10 second (240 frames) video for each time point and volunteer for assessment.

Image analysis (Lucida Analyse 4.0, Kinetic Imaging, Nottingham, UK) allowed the vascular content of each image to be calculated by tracing the area of blood vessels that were patent, recording both the patterns and percentage occupancy of each frame by vascular tissue. The mean vascularity per volunteer by time point was recorded and plotted. In addition, the use of real time imaging allowed each video sequence to be reviewed and deconstructed into its 24 frames per second constituent elements.

Figure 2:
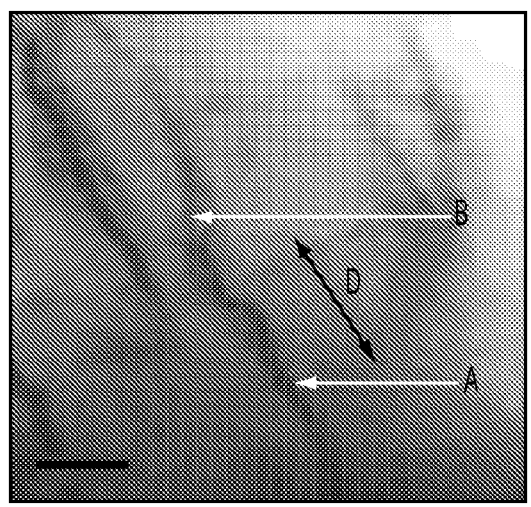

Constant frame size display allowed distance traveled per frame to substitute for flow rates and be comparable between subjects and over time. (See FIG. 2).

Results

In Vitro: Transmission Imaging

Figure 3:
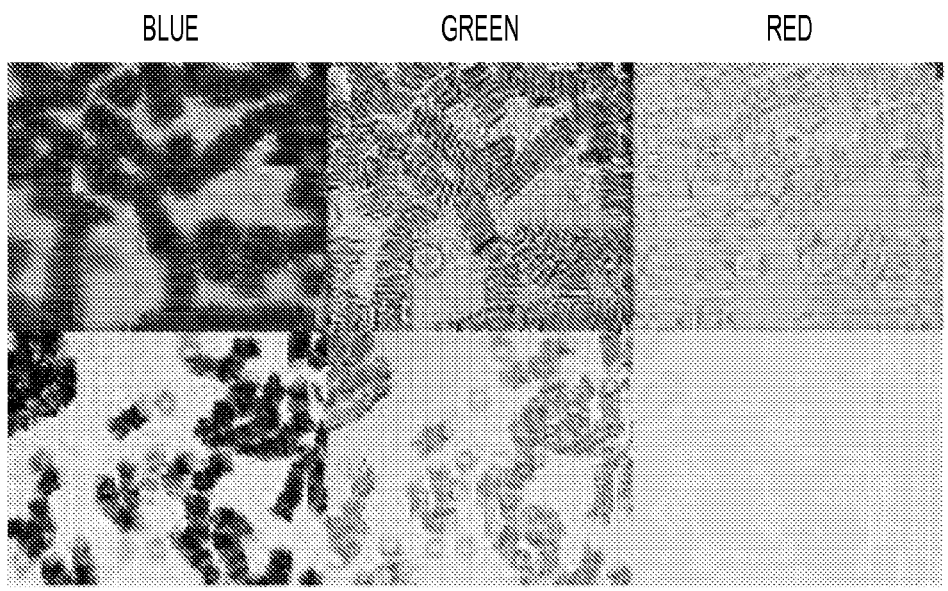

As expected, in transmission the haemoglobin within RBCs absorbed the shorter illumination wavelengths, producing darker cells in monochrome imaging while the contrast reduced, approaching background, in the longest wavelength. Only the optical effects of cell membrane phospholipid bilayers outlined the corpuscles in red illumination (FIG. 3).

The greyscale images employed an unbiased conversion to 256 grey levels in total; 0-255 reflecting black to white and images the single Cohu camera setting (without auto gain) ensured comparability. Differences in mean grey level from background and cell transmission showed similar contrast in the longer wavelengths while little contrast was seen in the longest wavelength chosen (Table 1). To allow for dissimilar energies at each wavelength, the cell and background grey level differences were normalised to the blue wavelength energy by comparison of the darkest (lowest greyscale value) areas sampled (0.94736=Dark in Blue/Dark in Green: 1.31411=Dark-Blue/Dark-Red)—showing identical absorption patterns, despite the detector energies undoubtedly varying with illuminating wavelength (Table 1).

TABLE 1

| Field illumination wavelengths All imaged x60/1.4na oil lens. | Mean & SD of 10 grey levels of background. | Mean & SD of 10 grey levels of cells. | Grey level difference between background and cells. | Grey level difference between background and cells after wavelength Correction to Blue-436 nm energy. |
|---|---|---|---|---|
| 436 nm-Blue | 238.55 (2.13668) | 213.946 (2.28335) | 24.604 | 24.604 |
| 518 nm Green | 251.804 (1.30742) | 224.932 (2.28393) | 26.872 | 25.457 |
| 600 nm Red | 181.53 (1.59937) | 180.482 (1.54174) | 1.048 | 1.377 |

Table 1: The RBCs appear darker with blue and green epi-illumination than red. The contrast between their content (Hb) against the background is significantly less for the red wavelength. Values relate to mean intensity grey levels and comparison of values between cell and background is given both as raw data and as normalised to blue illumination to account for variation in energies arriving at the detector from different wavelengths.

Reflection Model Imaging Configuration

Figure 4:
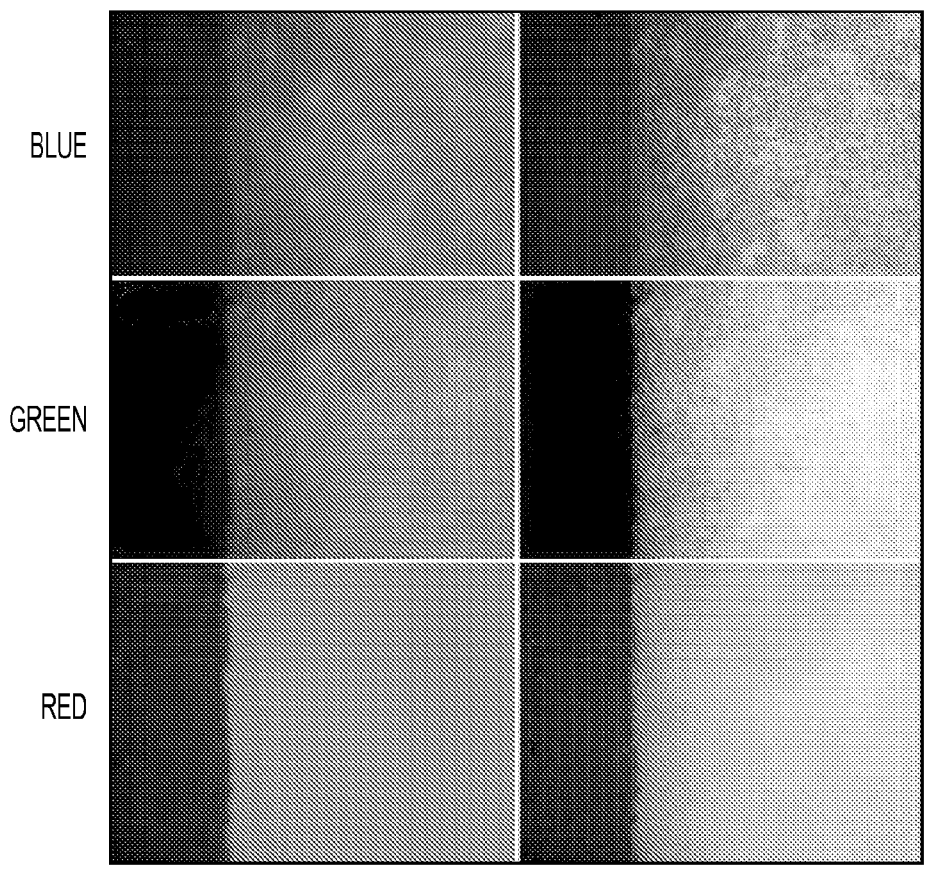

When imaged in reflection on the half-reflecting/half-absorbing slide surface, the same red cell absorption patterns in shorter illumination wavelengths were noted against the white reflective background (FIG. 4). Both Cells and background were consistently black (Hounsfiled values less than 25) indicating that deeper surface and tissue reflection and consequently cell trans-illumination effects explain the original in vivo reflection imaging from Watson et al 2002 (8). Cell outlines were barely visible, even when the X100/1.3na magnification objective was used, suggesting that any internal reflection mechanisms from the cell membranes was insignificant—particularly in the lower magnification and numerical aperture systems involved in the in vivo endoscopy setup. Whether the trans-illumination effects are two pass from light reflected directly on axis through a cell or reflected obliquely through a cell on the return to the detector from deeper reflecting surface, remains unknown. As shown in Table 2, the comparison of mean background to cell grey levels by wavelength showed loss of contrast at longest wavelength, the contrast being similar at shorter wavelengths. The pattern was retained in normalised format (0.69768=Dark-Blue/Dark-Green: 0.70304=Dark-Blue/Dark-Red) as previously employed in transmission mode (Table 2). No cell outlines and therefore contrasts were discernable against the black background.

TABLE 2

| Field illumination wavelengths All imaged x60/1.4na oil lens. | Mean & SD of 10 grey levels of background. | Mean & SD of 10 grey levels of cells. | Grey level difference between background and cells. | Grey level difference between background and cells after wavelength Correction to Blue-436 nm energy. |
|---|---|---|---|---|
| BLUE (436 nm) | 60.3301 (1.33568) | 43.2952 (1.32313) | 17.0349 | 17.0349 |
| GREEN (518 nm) | 86.4721 (1.51121) | 66.8916 (1.47235) | 19.5805 | 13.6609 |
| RED (600 nm) | 85.8131 (1.49087) | 77.2436 (1.20937) | 8.5695 | 6.0247 |

Table 2: The RBCs contrasts against background are maintained in reflection imaging against a bright surface shorter wavelengths are used. Transmission of reflected red light yields significantly reduced difference in mean intensity grey levels, even when corrected to blue light energy levels.

In Vivo Endoscopy Findings

Figure 5:
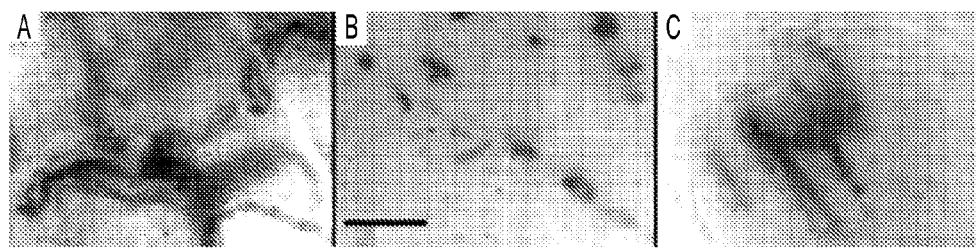

In vivo RBCs circulating in blood vessels appeared as black dots and clearly defined the local vascular pattern. Imaging of the labial mucosa before injection of local anaesthetic showed a mixture of deep feeder vessels of large diameter clearly defined and passing on to more superficial capillary vessels that would multiply twist forming a distal loop at the end for return flow (FIG. 5). Similar patterns were noted when buccal and sublingual mucosae were imaged. However, in keratinised mucosa, typified by the attached gingivae and hard palate, pinpoint tips of capillary loops only were visible—presumably as they arose between epithelial rete processes. In the dorsal tongue papillae a third vascular pattern was noted; twisted capillaries originating from arcuate feeder vessels rising into the mucosal segments.

Figure 6:
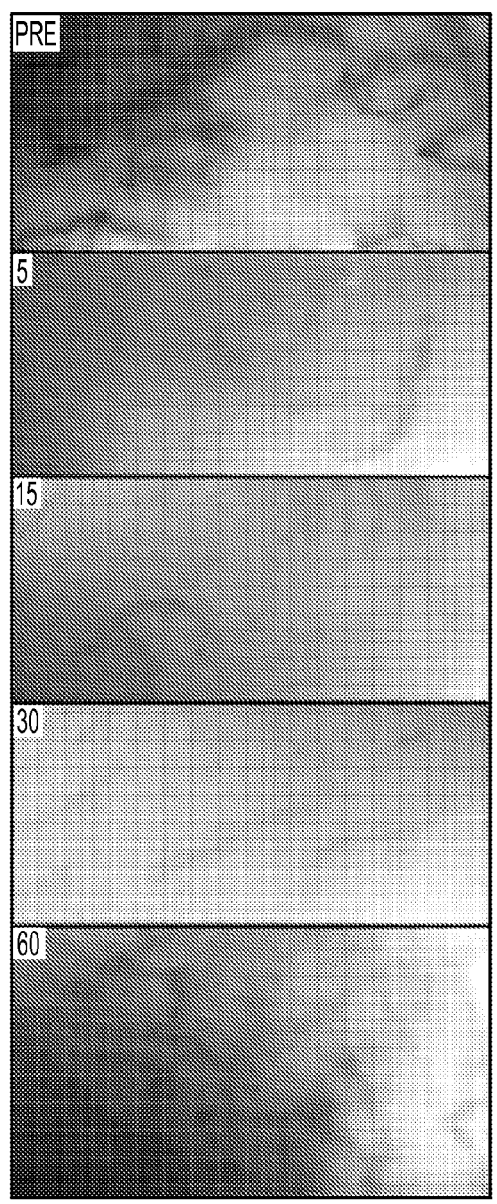

Imaging after vasoconstriction showed distinct changes in capillary and large vessel pattern (FIG. 6). As expected, a reversible adrenergic vasoconstriction effect was demonstrated after the local anaesthetic exposure. Interestingly, the deeper (muscular walled) arteriolar vessels shut down along with the majority of capillary loops, a few remaining patent, presumably providing baseline nutrition to the tissue.

Figure 7:
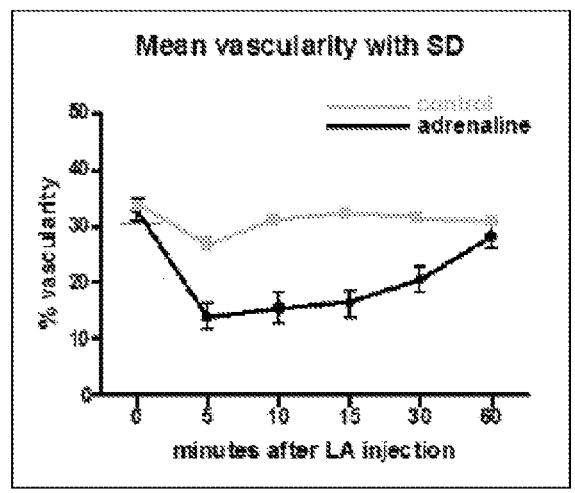

The mean change in image frame vascularity for all subjects at pre- and each post injection time is shown in FIG. 7 for all the volunteers and the control subject, in whom there was an equi-volumetric injection of saline alone. The mean reduction of image frame vascular occupation was approximately 62.2% of baseline levels when the local was introduced—as opposed to a 17.63% reduction in the control data. An early recovery between the 5th and 10th minute in the control returns vascular levels nearly to normal levels, whereas in the active group the suppression of vascular supply is maintained, rising towards normal between the 30th and 60th minute. Unpaired t-tests of normalised data show that the variances in vascularity are significantly different between the LA subjects and the control. The small initial reduction in the control vascularity is probably due to the local tissue trauma and tension in the corium introduced by insertion of the 27 gauge needle, even though lip tissue is relatively lax.

Figure 8:
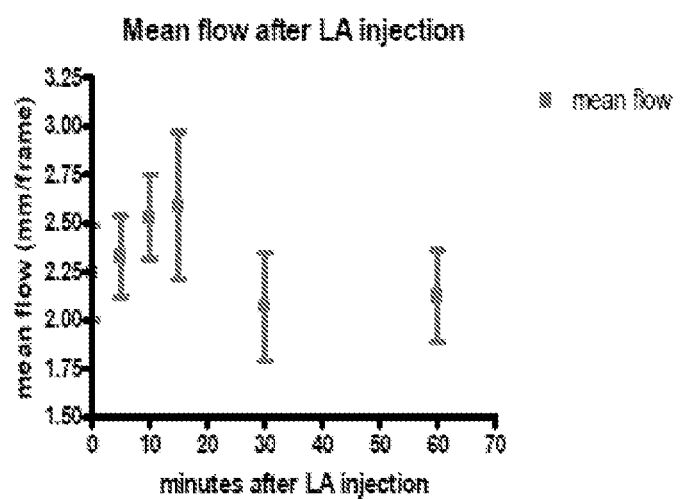
FIG. 8 shows variation in RBCs flow within the capillaries over time after exposure to adrenergic vasoconstrictor. A statistically insignificant increase was noted for most subjects within the first 10 minutes after injection; however the trend suggests flow remains stable regardless of adrenaline effect on these and deeper feeder vessels.

Real time imaging demonstrated RBC flow in capillary arcades and data for all volunteers at all time points was collated and plotted as distance moved per frame (1/24th second) as a representative of flow rate (FIG. 8). Cumulative mean flow velocity data showed a tendency for marginally increased (statistically insignificant (unpaired t-test)) flow in the remaining patent capillaries, suggesting a local population of catecholamine insensitive vessels for baseline tissue support.

Discussion

Our results show that despite a reflection configuration, transmission imaging effects are involved in this technique, RBCs acting as pass filters in the illumination system. Illumination energy is reflected by deeper tissue planes and interfaces, only long visible wavelengths being transmissible through the overlying haemoglobin pigment. Imaging was not deep enough to include significant red muscle, whose myoglobin pigment may well exert the same effect if adequately trans-illuminated. This same effect is employed by the pulse oximeter, utilising the partial absorption of red and infrared wavelengths passing through a fingertip to establish patient oxygen saturation based on the red chromatic shift of oxygenated haemoglobin (34).

Imaging patterns confirmed distinct capillary/small vessel patterns throughout the oral mucosa as Yao et al. found in the stomach (13). Also the expected principle contraction and loss from image of the smooth muscle walled arterioles, the primary regulators of blood flow, as a total absence of capillary networks was never seen. The graphical plot of the adrenergic vasoconstrictive effect confirms the surgical consensus that a relatively avascular field is achieved by local anaesthetics containing adrenaline for approximately 45 minutes, whereas the analgesic effect lasts another two hours.

In spite of the arterioles' shut down, total stasis was not observed indicating a minimal sustaining flow rate was maintained through involved tissues. Discontinuous imaging can only indicate flow trends; an anaesthetised preparation could confirm absolute values, flow reversals and shunting in a particular capillary bed over time. As an endoscope provides the distal optics, minimal surgical access techniques can also allow this type of instrumentation to be adapted for organ blood flow assessment experiments, with minimal tissue disturbances (33).

Fukui et al (2006) showed that gastric tumour microvessels behaving differently from normal mucosa microcirculations in response to adrenaline stimulation, providing an important impetus to further examine the behaviour of oral—usually squamous cell—carcinoma vasculatures (20).

Otsuka et al and Sugano et al (2004) and Ohashi et al (2005), report the value of microscopic assessments to compliment their vascular imaging, finding that the structure of early gastric lesions could be correlated to vascular architecture and lesion margins could be identified without tissue biopsy. These results are promising for possible early detection and differentiation between gastric lesions (4; 17; 18).

Traditionally, the diagnosis of most oral lesions is based on clinical signs and symptoms as well as histopathological features, requiring a surgical procedure (biopsy). In the case of vascular lesions such as haemangiomas, haematomas and Kaposi sarcomas, the biopsy involves the risk of significant postoperative bleeding and infection. In most of these cases, and especially in the immunocompromised patient, the biopsy presents additional hazards of bleeding and cross infection to surgical staff and is avoided if possible; the diagnosis being mainly based on clinical knowledge and experience alone in these cases. Therefore the development of non-invasive diagnostic techniques and instruments is of significant benefit for the diagnosis of vascular lesions alone and may well contribute to the non-surgical characterisation of tumours in the future.

In the case of vascular lesions a congenital or malignancy-driven change in the conventional vascular pattern of each anatomical area occurs, depending on the nature of each lesion. The development of an instrument that uses the contrast effect of Hb in order to provide real time in vivo images of a vascular lesion, non-invasively and with no need of prior labelling or any other preparation, could prove of tremendous benefit in the diagnosis of vascular lesions, the identification of tumour neo vascularisation as well as the response to treatment.

In this instrument application, the confocal disk microscope played no direct role other than acting as a neutral density filter in the non-confocal imaging path.

Figure 9:
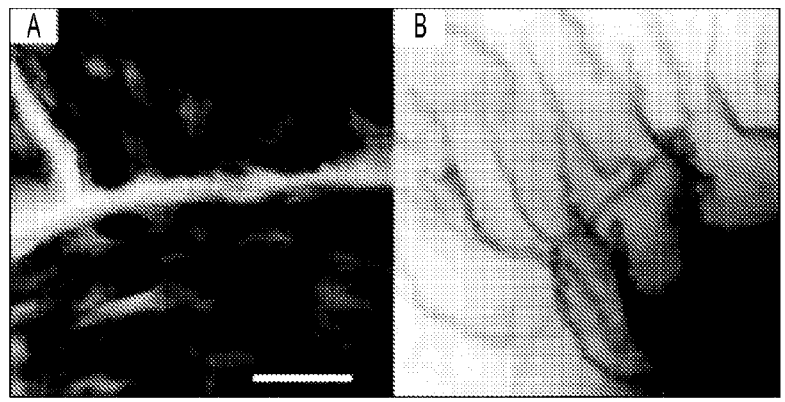
FIG. 9 shows a near synchronous fluorescence (A) view (0.25% fluorescein(aq) topical) on nonkeratinised oral mucosa and (B) in 540 nm epi-illumination the subjacent vasculature is imaged as expected for normal overlying oral mucosa. 800 nm field widths.

However, the instrument design did not compromise the confocal instrument's integrity and with the aid of topical fluorescein, 488 nm surface fluorescence confocal imaging of the overlying epithelium in the lip was also undertaken in a single volunteer, showing an instrument capable of imaging both the underlying vascular architecture and the overlying labial epithelium (from which cancers are derived by definition) by near concurrent imaging. The two systems were previously shown to defeat each other if conducted simultaneously (8) but do provide a mechanism for near synchronous surface and sub-surface vascular tissue examination without surgical intervention.(11) (FIG. 9).

Biopsy remains the current gold standard supplement for clinical examination in upper aerodigestive tract lesion diagnosis; exfoliative cytology and vital staining techniques carrying potentially high false positive rates (35 36). Upile et al. report stretching buccal mucosa to reveal uniform nuclear arrangements in methylene blue chemo endoscopic oral mucosal examinations, citing the advantage of real time dynamic imaging in reporting/surveying field changes and better localising clinical resection margins. Dysplasia and carcinoma in situ are the conventional heralds of oral cancer development but often carcinoma develops without clinically noted dysplastic features—possibly through speed of change (37). Vascular pattern imaging may well permit detection of field changes and more timely cellular examination and intervention. Natural ab-basal migration of epithelial cells suggests micro-endoscopy and sectional surface imaging have an important joint role in the detection and delineation of underlying epithelial pathologies (37).

EXAMPLE 2

A hand-held device which allows the direct imaging of the capillary structure directly under the skin and maps the precise blood oximetry across this capillary structure with unprecedented lateral resolution. This device is based on the reflection and spectral analysis by the fatty layer of a white light illumination of the skin via a solid endoscope. The light collected back by the solid tube is separated at three different stages by carefully-selected dichroic filters before being focused and imaged on three different CCD cameras.

The first filtering stage (D1 FIG. 10) separates the green and yellow components of the reflected light from the longer wavelengths (which go through the next filtering stage). This green-yellow light correspond to the strong haemoglobin absorption peak and allows us to directly image the capillary structure between the skin and the fatty tissue.

The second stage (D2 FIG. 10) separates the remaining light into its red and infrared components which are then individually imaged onto separate CCD cameras optimised at each wavelength. The ratio between these two signals is then calculated in a similar fashion as pulse oximetry to obtain an instantaneous measurement of the blood oxygen content.

This method allows use to obtain two different maps of the blood vessels lying under the skin: the first map shows directly the position of individual capillaries while the second map gives an oximetry reading along each of them. The fast data acquisition of current state-of-the art CCD camera allows each map to be obtained in real time with unprecedented optical resolution. Further real-time post-processing on a very fast computer of each image pixel allows us to apply the current pulse oximetry algorithms and obtain ultra-accurate oxygenation measurement at each position across the image. In order to ensure comfortable operation of the device in a hospital environment, a light and compact design is required. This will be achieved with a precise combination of precision optics and small form factor cage assembly supported by short-sized metal linkers. In our design, each filtering stage is embedded within a linker cube and comprise of the right selection of dichroic filter and band pass filter. In this configuration, each CCD camera is positioned at 90 degree from each others and within an inch from the device axis. At the front of the device, a commercial solid endoscope, including an integrated optical fibre light delivery system, is directly mounted along the main optical axis of the device. This configuration allows for the light source to be located remotely, ensuring the lightest possible weight for comfort utilisation: the light source and the computer, necessary for processing and display, are located remotely with only the optical fibre along with the CCD camera control wires attached to the device.

REFERENCES (1) Hoffman A, Kiesslich R, Bender A, Neurath M F, Nafe B, Herrmann G et al. Acetic acid-guided biopsies after magnifying endoscopy compared with random biopsies in the detection of Barrett's esophagus: a prospective randomized trial with crossover design. Gastrointest Endosc 2006; 64(1):1-8.
(2) Cotton & Williams. Practical Gastrointestinal endoscopy. London: Blackwell Scientific, 1996: 1-11.
(3) Suzuki S, Murakami H, Suzuki H, Sakakibara N, Endo M, Nakayama K. An endoscopic staining method for detection and operation of early gastric cancer. Int Adv Surg Oncol 1979; 2:223-241.
(4) Sugano K, Sato K, Yao K. New diagnostic approaches for early detection of gastric cancer. Dig Dis 2004; 22(4):327-333.
(5) Kumagai Y, Inoue H, Nagai K, Kawano T, Iwai T. Magnifying endoscopy, stereoscopic microscopy, and the microvascular architecture of superficial esophageal carcinoma. Endoscopy 2002; 34(5):369-375.
(6) Inoui H, Kudo S, Shiokawa A. Laser scanning confocal microscopy and endocytoscopy for cellular observations of the gastrointestinal tract. Gastroenterology and Hepatology 2005; 31-35.
(7) Kumagai Y, Michio I, Yamazaki S. Magnifying endoscopic observations of the upper gastrointestinal tract. Digestive Endoscopy 2006; 18:165-172.
(8) Watson T F, Neil M A A, Juskaitis R, Cook R J, Wilson T F. Video rate confocal Endoscopy. Journal of Microscopy 2002; 207:37-42.
(9) Abe S, Izuishi K, Tajiri H, Kinoshita T, Matsuoka T. Correlation of in vitro autofluorescence endoscopy images with histopathologic findings in stomach cancer. Endoscopy 2000; 32(4):281-286.
(10) Bhunchet E, Hatakawa H, Sakai Y, Shibata T. Fluorescein electronic endoscopy: a novel method for detection of early stage gastric cancer not evident to routine endoscopy. Gastrointest Endosc 2002; 55(4):562-571.
(11) Watson A P, Rosen E S. Oral fluorescein angiography: reassessment of its relative safety and evaluation of optimum conditions with use of capsules. Br J Opthalmol 1990; August; 74(8):458-461.
(12) Andrea M, Santos Dias O. Contact endoscopy during micro-laryngeal surgery. A new technique for the endoscopic examination of the larynx. Ann Oto Rhino Laryngol 1995 104 333-339.)
(13) Yao K, Iwashita A, Kikuchi Y, Yao T, Matsui T, Tanabe H et al. Novel zoom endoscopy technique for visualizing the microvascular architecture in gastric mucosa. Clin Gastroenterol Hepatol 2005; 3(7 Suppl 1):S23-S26.
(14) Yao K, Yao T, Matsui T, Iwashita A, Oishi T. Hemoglobin content in intramucosal gastric carcinoma as a marker of histologic differentiation: a clinical application of quantitative electronic endoscopy. Gastrointest Endosc 2000; 52(2):241-245.
(15) Yao K, Oishi T, Matsui T, Yao T, Iwashita A. Novel magnified endoscopic findings of microvascular architecture in intramucosal gastric cancer. Gastrointest Endosc 2002; 56(2):279-284.
(16) Tajiri H, Doi T, Endo H, Nishina T, Terao T, Hyodo I et al. Routine endoscopy using a magnifying endoscope for gastric cancer diagnosis. Endoscopy 2002; 34(10):772-777.
(17) Otsuka Y, Niwa Y, Ohmiya N, Ando N, Ohashi A, Hirooka Y et al. Usefulness of magnifying endoscopy in the diagnosis of early gastric cancer. Endoscopy 2004; 36(2):165-169.
(18) Ohashi A, Niwa Y, Ohmiya N, Miyahara R, Itoh A, Hirooka Y et al. Quantitative analysis of the microvascular architecture observed on magnification endoscopy in cancerous and benign gastric lesions. Endoscopy 2005; 37(12):1215-1219.
(19) Hiki Y. Endoscopic diagnosis of mucosal cancer. Semin Surg Oncol 1999; 17(2):91-95.
(20) Fukui H, Shirakawa K, Nakamura T, Suzuki K, Masuyama H, Fujimori T et al. Magnifying pharmacoendoscopy: response of microvessels to epinephrine stimulation in differentiated early gastric cancers. Gastrointest Endosc 2006; 64(1):40-44.
(21) Tsuji S, Kawano S, Hayashi N, Tsujii M, Ogihara T, Kamada T et al. Analysis of mucosal blood hemoglobin distribution in gastric ulcers by computerized color display on electronic endoscopy. Endoscopy 1991; 23(6):321-324.
(22) Nakayoshi T, Tajiri H, Matsuda K, Kaise M, Ikegami M, Sasaki H. Magnifying endoscopy combined with narrow band imaging system for early gastric cancer: correlation of vascular pattern with histopathology (including video). Endoscopy 2004; 36(12):1080-1084.

(23) Pazouki S, Chisholm D M, Adi M M, Carmichael G, Farquharson M, Ogden G R et al. The association between tumour progression and vascularity in the oral mucosa. J Pathol 1997; 183(1):39-43.
(24) Macluskey M, Chandrachud L M, Pazouki S, Green M, Chisholm D M, Ogden G R et al. Apoptosis, proliferation, and angiogenesis in oral tissues. Possible relevance to tumour progression. J Pathol 2000; 191(4):368-375.
(25) Tipoe G L, Jin Y, White F H. The relationship between vascularity and cell proliferation in human normal and pathological lesions of the oral cheek epithelium. Eur J Cancer B Oral Oncol 1996; 32B(1):24-31.
(26) El-Gazzar R, Macluskey M, Ogden G R. Evidence for a field change effect based on angiogenesis in the oral mucosa? A brief report. Oral Oncol 2005; 41(1):25-30.
(27) Jin Y, Tipoe G L, White F H, Yang L. A quantitative investigation of immunocytochemically stained blood vessels in normal, benign, premalignant and malignant human oral cheek epithelium. Virchows Arch 1995; 427(2):145-151.
(28) Dunstan S, Powe D G, Wikinson M, Pearson J, Hewitt R E. The tumour stroma of oral squamous cell carcinomas show increased vascularity compared with adjacent host tissue. Br J Cancer 1997; 75(4):559-565.
(29) Shieh Y S, Lee H S, Shiah S G, Chu Y W, Wu C W, Chang L C. Role of angiogenic and non-angiogenic mechanisms in oral squamous cell carcinoma: correlation with histologic differentiation and tumor progression. J Oral Pathol Med 2004; 33(10):601-606.
(30) Carlile J, Harada K, Baillie R, Macluskey M, Chisholm D M, Ogden G R et al. Vascular endothelial growth factor (VEGF) expression in oral tissues: possible relevance to angiogenesis, tumour progression and field cancerisation. J Oral Pathol Med 2001; 30(8):449-457.
(31) Tae K, El-Naggar A K, Yoo E, Feng L, Lee J J, Hong W K et al. Expression of vascular endothelial growth factor and microvessel density in head and neck tumorigenesis. Clin Cancer Res 2000; 6(7):2821-2828.
(32) Li C, Shintani S, Terakado N, Klosek S K, Ishikawa T, Nakashiro K et al. Microvessel density and expression of vascular endothelial growth factor, basic fibroblast growth factor, and platelet-derived endothelial growth factor in oral squamous cell carcinomas. Int J Oral Maxillofac Surg 2005; 34(5):559-565.
(33) Upile T, Jerjes W, El Maaytah M, Hopper C, Searle A, Wright A. Direct microvascular monitoring of a free autologous jejunal flap using microendoscopy: a case report. BMC Ear Nose & Throat Disorders 2006 6 (14) doi: 10.1186/1472-6815-6-14.
(34) Fearnley S J. Pulse Oximetry. Practical Procedures 1995; issue 5:article 2:1.
(35) Upile T, Fisher C, Jerjes W, El Maaytah M, Singh S, Sudhoff H, Searle A, Archer D, Michaels L, Hopper C, Rhys-Evans P, Howard D, Anthony Wright A. Recent technological developments: in situ histopathological interrogation of surgical tissues and resection margins. BMC Head & Face Medicine 2007 3 (13) doi: 10.1186/1746-160X-3-13.
(36) Silverman S Jr, Dillon W P. Diagnosis in Oral Cancer 3rd Edn. Churchill Livingstone London 1982 pp 21-31.
(37) Silverman S Jr, Gorsky M, Lozada F. Oral leukoplakia and malignant transformation. A follow up study of 257 patients Cancer 1984 53 563-568.

The invention claimed is:

1. An imaging apparatus for imaging the vasculature of an organ or tissue and mapping the blood oximetry across the vasculature, the apparatus comprising: a light source for illuminating the organ or tissue;
  a lens mounted within a housing to collect light from the illuminated organ or tissue;
  a first optical filter to separate green wavelengths from the light;
  a second optical filter to separate red wavelengths in the light from infrared wavelengths in the light, or to separate red wavelengths in the light from blue wavelengths in the light; and
  image capturing devices to image each of the green wavelengths, the red wavelengths and the infrared wavelengths of the collected light, or to image each of the green wavelengths, the red wavelengths and the blue wavelengths of the collected light, wherein the apparatus allows the blood oximetry of the vasculature to be mapped.

2. The imaging apparatus of claim 1 for imaging the capillaries of an organ or tissue.

3. The imaging apparatus of claim 1, wherein the green, red and infrared images; or the green, red and blue images are measured simultaneously.

4. The imaging apparatus of claim 1, wherein the light source emits at least green, red and blue light.

5. The imaging apparatus of claim 4, wherein the light source does not emit infrared light.

6. The apparatus of claim 1, wherein the apparatus has been calibrated so that the images can be overlaid to align corresponding points in each image to allow calculation of the oxygenation and assignment of that oxygenation value to a particular point on the vasculature.

7. The imaging apparatus of claim 1, further comprising a third optical filter.

8. The imaging apparatus of claim 1, wherein the filters are dichroic filters.

9. The imaging apparatus of claim 1, wherein the image capturing devices are CCD cameras.

10. The imaging apparatus of claim 1, wherein the image capturing devices are connected to a computer to calculate the oxygenation of the vasculature using the red and infrared images.

11. The imaging apparatus of claim 1, wherein the lens mounted within a housing is an endoscope.

12. The imaging apparatus of claim 11, wherein the light source illuminates the tissue or organ via the endoscope.

13. The imaging apparatus of claim 1, wherein the light source is positioned at a distance from the lens and the organ or tissue and light is transmitted to the organ or tissue by a light guide.

14. The imaging apparatus of claim 13, wherein the lens mounted within a housing is an endoscope and the light guide is positioned within the endoscope.

15. A method for imaging the vasculature of an organ or tissue and mapping the blood oximetry across the vasculature, the method comprising:
  illuminating the organ or tissue;
  collecting the light from the organ or tissue;
  separating the green, red and infrared wavelengths in the light, or separating the green red and blue wavelengths in the light;
  imaging each of the green, red and infrared wavelengths of the light or imaging each of the green, red and blue wavelengths of the light; and calculating the oxygenation of the vasculature using the red and infrared images, or red and blue images.

16. The method of claim 15 wherein the capillaries of an organ or tissue are illuminated.

17. The method of claim 15, wherein the green, red and infrared images; or the green, red and blue images are measured simultaneously.

18. The method of claim 15, wherein the light source emits at least green, red and blue light.

19. The method of claim 18, wherein the light source does not emit infrared light.

20. The method of claim 15, wherein the ratio between the red and infrared images, or the ratio between the red and blue images is calculated to determine the oxygenation of the vasculature.

21. The method of claim 15, further comprising a step of calibrating the imaging process so that the images can be overlaid to align corresponding points in each image to allow calculation of the oxygenation and assignment of that oxygenation value to a particular point on the vasculature.

22. The method of claim 15, wherein the green, red and infrared wavelengths of the light, or the green, red and blue wavelengths of the light are imaged using CCD cameras.

23. The method of claim 15, wherein the oxygenation of the vasculature is calculated using a computer.

24. The method of claim 15, wherein the light is collected using an endoscope.

25. The method of claim 24, wherein the organ or tissue is illuminated via the endoscope using a light source.

* * * * *

UNITED STATES PATENT AND TRADEMARK OFFICE
CERTIFICATE OF CORRECTION

PATENT NO. : 8,364,222 B2
APPLICATION NO. : 12/678646
DATED : January 29, 2013
INVENTOR(S) : Cook et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 450 days.

Signed and Sealed this
First Day of September, 2015

Michelle K. Lee
*Director of the United States Patent and Trademark Office*